United States Patent
Hoffman et al.

(10) Patent No.: US 6,268,145 B1
(45) Date of Patent: Jul. 31, 2001

(54) SCREENING TEST FOR THE LETHAL GENETIC TRAIT OF RECURRENT SPONTANEOUS PREGNANCY LOSS

(75) Inventors: Eric P. Hoffman, Kensington, MD (US); Mark C. Lanasa; W. Allen Hogge, both of Pittsburgh, PA (US)

(73) Assignees: Children's National Medical Center, Washington, DC (US); University of Pittsburgh, Pittsburg, PA (US)

( * ) Notice: Subject to any disclaimer, the term of this patent is extended or adjusted under 35 U.S.C. 154(b) by 0 days.

(21) Appl. No.: 09/401,777

(22) Filed: Sep. 22, 1999

(51) Int. Cl.[7] .................................................. C12Q 1/68

(52) U.S. Cl. .................. 435/6; 435/6; 435/91.1; 435/91.2; 424/93; 436/811

(58) Field of Search ............................ 435/6, 91.1, 91.2; 424/93; 436/811

(56) References Cited

PUBLICATIONS

Lanasa et al Am J Hum Gen. 65(1):252–4 (Jul. 1999).
Pegoraro et al. Am J Hum Gen 61(1):160–70 (Jul. 1997).
Sangha et al., Am J Hum Gen 65:913–17 (1999).
Pegoraro et al. Am J Hum Gen, 54:989–1003 (1994).
Lanasa et al. Am J Hum Gen, 64: 934–38 (1999).

*Primary Examiner*—W. Gary Jones
*Assistant Examiner*—Janell E. Taylor
(74) *Attorney, Agent, or Firm*—Melvin Blecher

(57) ABSTRACT

A screening test to identify women carrying a lethal genetic trait that predisposes to recurrent spontaneous pregnancy loss. The test method involves the quantitative determination of the frequency of highly skewed X chromosome inactivation in DNA derived from tissue cells of female patients, relative to appropriate normal control women. "Highly skewed" is defined as preferential use of one chromosome in at least 90% of the patient's cells being tested. Suitable test tissues include, but are not limited to, peripheral leukocytes, oral mucosal cells, and biopsy material.

7 Claims, 1 Drawing Sheet

SCREENING TEST FOR THE LETHAL GENETIC TRAIT OF RECURRENT SPONTANEOUS PREGNANCY LOSS

SUBJECT OF THE INVENTION

The invention is concerned with a screening method for diagnosing the etiology of spontaneous pregnancy loss in women. More particularly, the inventive method involves the use of quantitative X chromosome inactivation analysis for the prediction of the presence of gene-linked recurrent spontaneous pregnancy loss.

BACKGROUND OF THE INVENTION

Recurrent spontaneous abortion (RSA) is a major health concern to women, affecting about 17% of couples wishing to have children. The diagnostic evaluation of RSA is extensive and complex, with many different etiologies, each causing a small proportion of the total cases. The etiologies can be grouped into five categories: anatomic, infectious, hormonal, immunological, and genetic, thereby requiring the collaborative efforts of many medical specialists. Despite such thorough (and expensive) diagnostic workups, it has been estimated that the specific cause for RSA remains unknown in 37–79% of affected women (Stephenson, Fertil. Steril. 66:24 (1996)).

It has been assumed that a large portion of idiopathic RSA is genetic in origin. To date, however, the standard genetic evaluation consists solely of parental and abortus karyotyping. This identifies parental defects, such as balanced translocations that can cause RSA, and it ascertains fetal aneuploidy, a common cause of spontaneous abortion that intrinsically has little recurrence risk. As a result, the published total "genetic" contribution to RSA is essentiually the frequency of translocations in the cohort of women with RSA, which is only about 3%. This is quite likely an underestimation, as subcytogenetic defects are almost certainly a significant cause of RSA.

It is possible that either autosomal or X-linked recessive lethal traits could cause RSA. Identification of recessive lethal traits has been difficult, as heterozygous carriers of such traits would appear phenotypically normal. A subset of lethal traits may cause an increased frquency of spontaneous abortions in carriers, if the X-linked hemizygous trait produces a clinically detectable pregnancy. Extended pedigrees in which women exhibit spontaneous abortion are available, but are difficult to analyze, because of the high population prevalence of spontaneous abortion and the assumed extensive genetic and etiologic heterogeneity. Thus, a method for clinically ascertaining carriers of autosomal lethal defects for recurrent spontaneous pregnancy loss remains problematical, although higly desirable.

There have been many efforts to characterize single genes that may cause miscarriage. However, there are approximately 100,000 genes in the human genome, which makes the search for such a single gene an almost intractable problem.

The present inventors have investigated the possibility that carriers of X-linked recessive lethal traits for recurrent spontaneous abortion manifest the molecular phenotype of nonrandom (skewed) X chromosome inactivation, and have invented a screening test for identifying and diagnosing a subset of women with recurrent spontaneous abortions. The test is based on a quantitative determination of the frequency of skewed X chromosome inactivation. This novel test, which is described below, can identify a lethal defect in a significant percentage of all of the genes in a woman. In essence, the test allows many of the lethal gene defects in the human genome to be surveyed at one time.

SUMMARY OF THE INVENTION

The screening test method of the invention provides for the identification and establishment of the risk for women who carry an X-linked lethal gene which increases their risk of recurrent spontaneous pregnancy loss.

The inventive test involves the quantitative determination in female subjects of the frequency of highly nonrandom (skewed) X chromosome inactivation, compared to that of appropriate control women.

The inventive test method is performed on DNA extracted from readily available cells from subjects, including, but not limited to, peripheral blood leukocytes, oral mucosal cells, muscle biopsies, or any other appropriate tissue.

These and other aspects of the invention will become apparent by reference to the specification and claims below.

DESCRIPTION OF THE PREFERRED EMBODIMENTS

Predictive Model

Figure 1:
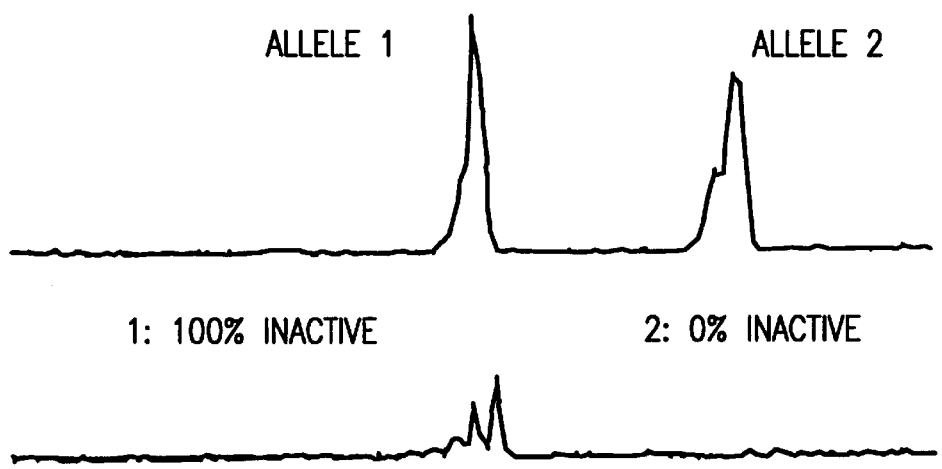
FIG. 1 is a trace of X chromosome inactivation patterns in patient's cell DNA by means of fluorescent PCR.

For the purposes of this application, "highly skewed (nonrandom) X-chromosome inactivation" is defined as follows. The X chromosome is unique in that it undergoes transciptional silencing (inactivation) to achieve sex-independent dosage equilibrium of most X-linked genes. X inactivation occurs early in embryogenesis, at the 64 to 100-cell stage. It is thought to be a stochastic event, that is, each cell is equally likely to inactivate either the maternal or paternal allele, and the choice of alleles is not influenced by neighboring cells. Therefore, in normal females, approximately half the cells transcribe genes on the maternally inherited X-chromosome, and the other half transcribe genes on the paternally inherited X chromosome.

Given this feature of X chromosome inactivation, it is unusual to find women with nonrandon (skewed) X inactivation, that is, the preferential use of either the maternally inherited or paternally inherited allele in a preponderance of that female's cells. When this phenomenon is observed, it may be associated with a defect on one of the X chromosomes.

The present inventors suggest that this model of cell selection during embryonic development, which also yields skewed X inactivation in an X:autosome translocation carrier, predicts that functional hemizygosity for even a single vital X-linked gene would also yield skewed X inactivation in a female carrier. Such a carrier may be spared any clinical phenotype, but, as the result of the selection against those cells missing the vital gene, she would manifest the the molecular phenotype of skewed X inactivation. All males are hemizygous for genes on the X chromosome and male pregnancies inheriting the maternal X chromosome with the lethal gene, would not be viable and would spontaneously abort sometime after conception. The inventors predict that, as such, female carriers of X-linked lethal traits will show extremely skewed X chromosome inactivation and may have recurrent pregnancy loss of a male fetus as a result. As these women would abort half of all male embryos their risk of spontaneous abortion increases from a population risk of 15% to a combined risk of up to 40% (15%+25%), assuming that carriers of X-linked lethal traits do not constitute a major proportion of all femsales who experience single pregnancy losses.

Invention Based on Model

Based on their testing of the model, the inventors have invented, and reduced to practise, a screening test for determining if women with recurrent spontaneous abortion (a.k.a., pregnancy loss, miscarriage) are genetically predisposed to pregnancy loss due to an X-linked recessive lethal gene mutation.

The screening test method determines quantitatively the X-chromosome inactivation patterns in women, and is used to identify those women who are preferentially using one chromosome (skewed inactivation), relative to previously tested appropriate normal controls.

As used herein, "highly skewed" is defined as preferential use of one X chromosome in at least 90% of the tissue tested, e.g., peripheral leukocytes. Higher cut off points, e.g., at least 95%, may also be employed to increase even further the reliability of the conclusions from X chromosome inactivation analyses.

The screening test method is carried out on DNA extracted from any convenient cells from a subject. Such convenient cells include blood peripheral leukocytes (Pegoraro et al. *Am. J. Hum. Gen.* 54:989 1994)), oral mucosal cells (Pegoraro et al. *Neurology* 45:677 (1995), and cryopreserved muscle biopsies (see, e.g., Lawton et al., *J. Oral Pathol. Med.* 21:265 (1992); Vogelstein et al, *Cancer Res.* 47:4806 (1987); Miller et al., *Nucleic Ac. Res.* 16:1215 (1988); and Pegoraro et al., *Am. J. Hum. Gen.* 61:160 (1997)), although other tissues may also be used for this purpose. Details of standard methods for DNA extraction from tissues are provided in these references.

X-inactivation patterns in DNA extracted from tissues may be quantified by the use of fluorescent PCR as described elsewhere (Allen et al., *Am. J. Hum. Gen.* 51:1229 (1992); Pegoraro et al., 1994, Pegoraro et al. 1997). These procedures are summarized in Example 1, below.

Statistical analyses of X-inactivation results may be performed as described in detail in Pegoraro et al., 1997. This same reference also provides details of standard methods for hypervariable-repeat analyses, linkage analyses, cytogenetic analyses, and physical mapping of polymorphisms.

Additional embodiments, falling within the scope of the invention, may become apparent to the reader from the information provided herein.

EXAMPLES

Example 1

Laboratory Methods

DNA Extraction

Peripheral blood was collected in EDTA tubes, and DNA isolated from leukocytes, as described elsewhere (Pegoraro et al., 1994, above).

Muscle DNA was isolated from cryosections of muscle biopsies, as described elsewhere (Pegoraro et al., 1995, above).

To isolate oral (cheek) mucosal cellular DNA, mouthwashing was done for 30 s in about 10 ml of 3% sucrose, and the rinse collected in tubes containing 10 mM EDTA as a preservative. Cells were isolated from this suspension by centrifugation at 14,000×g for 20 min. Cells were solubilized in lysis buffer. Proteinase K digestion in PCR buffer was done at 60 C for 2 hr. Samples were extracted with phenol-chloroform and chloroform, and the DNA was concentrated by use of Amicon MICROCON microconcentrators.

X-chromosome Inactivation Method

X-inactivation patterns in the aforementioned DNA samples were quantified by the use of fluorescent PCR as described elsewhere (Allen et al., 1992, above; Pegoraro et al., 1994, above). In brief, the methylation status of the androgen receptor promoter adjacent to a highly polymorphic CAG repeat in the 5' end of the coding region of the androgen receptor gene was assessed by the use of methylation-sensitive restriction enzymes HpaII/C/oI). PCR products, both before and after digestion, were electrophoresed on an ABI 373A automated sequencer, and peak heights were analyzed by the use of GENESCAM software (Applied Biosystems). Corrections for preferential PCR of alleles, as well as spontaneous X inactivation, were done according to Pegararo et al., 1994, above. Ratios of at least 90%:10% were used as the cut off points to classify the patient as having a highly skewed X inactivation pattern.

Statistical analyses, cytogenetic analyses and physical mapping of DNA were done according to standard methods (Pegoraro et al., 1997, above).

Example 2

Association Between Idiopathic RSA and X Lethal Loci

A limited case-control study was done using the techniques described in Example 1, above. In this study the frequency of highly skewed X chromosome inactivation in women with two or more unexplained spontaneous abortions, was compared to female controls. In this study skewed X chromosome was defined as preferential use of one chromosome in greater than or equal to 90% of peripheral leukocytes, and assumed that such extreme skewing reflects the carrier state for X-linked lethal conditions.

It was found that 4 of 34 (11.7%) women with unexplained spontaneous abortions and one of 62 (1.6%) control women to have skewed X inactivation by these criteria. This represents a statistically significant odds ratio of 8.13 with 95% confidence limits of 55.9 to 1.18.

These data demonstrate that the X chromosome inactivation assay is a powerful method for ascertaining cell-autonomous X-linked recessive lethal defects. Identification of such women is of significant clinical and counseling benefit.

Example 3

Association Between Idiopathic RSA and X-linked Lethal Loci

In another study, similar to that described in Example 2, women characterized with a number of spontaneous abortions underwent a complete evaluation to rule out any of the known causes of RSA described above (Stephanson 1996, above). The tests performed were as follows: cytogenetic-parental and abortus karyotyping; anatomic-hysterosalpingogram; infections-cervical cultures for mycoplasma, ureaplasma, gonnococcus, and chlamydia; immunologic-anticardiolipin antibodies, antinuclean antibodies, and lupus anticoagulant; and, hormonal-serum progesterone, late luteal phase endometrial biopsy, and thyroid stimulating hormone.

The controls were women from the same demographic region with no known history of spontaneous abortion.

Further, the cases and controls were age-distribution matched, and the age distribution between the two groups was about the same.

Defining X inactivation as preferential use of one X chromosome in at least 90% of peripheral leukocytes, it was found that 7 (14.6%) of 48 subjects had skewed X chromosome inactivation (Table 1, FIG. 1), and only 1 (1.5%) of 68 control females demonstrating such inactivation (Table 1). This result is statistically significant (P<0.01). The distribution ratios for both cases and controls are shown in FIG. 2.

TABLE 1

X Chromosome Inactivation Tests in Women with Recurrent Spontaneous Abortion

| Category | X Inactivation Skewed >90% n (%) | Random | Total |
|---|---|---|---|
| RSA cases | 7 (14.6) | 41 | 48 |
| Controls | 1 (1.5) | 66 | 67* |

* P < .01

Figure 2A:
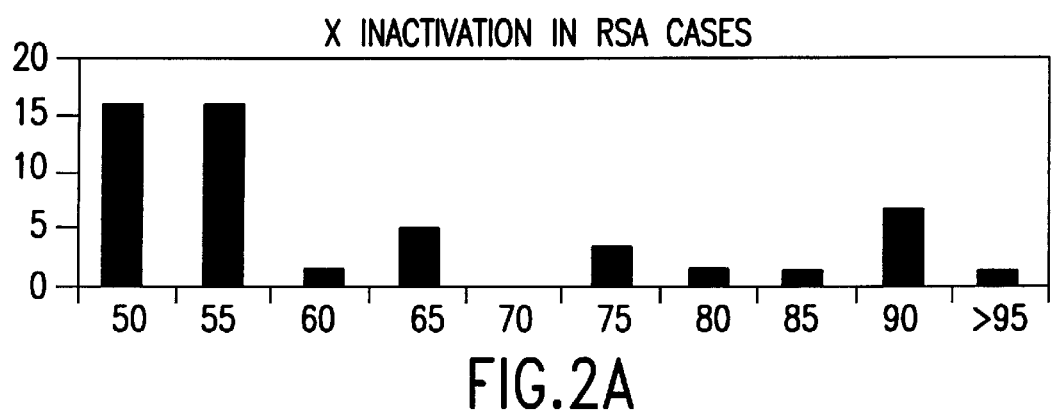
FIG. 2 is a graphical representation of X chromosome inactivation data in female subjects.
Figure 2B:
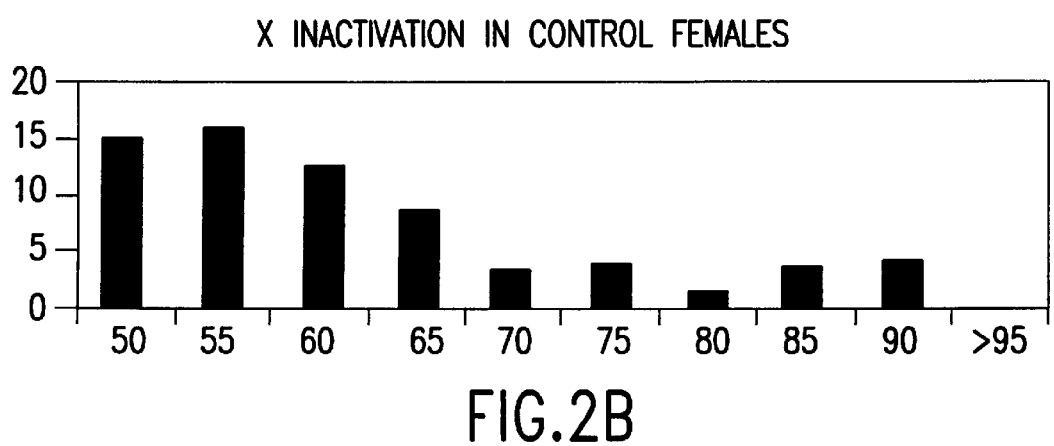

The skewing of X chromosome inactivation in RSA is shown in FIG. 1. Genomic DNA samples from women with RSA were subjected to PCR amplification of highly polymorphic HUMARA locus with fluorescent primers. One gravida5para0 (G5PO) woman was heterozygous at this locus (upper trace). Digestion of genomic DNA with methylation-sensitive restriction enzymes prior to PCR at the HUMANA locus permitted accurate quantitation of x-inactivation patterns (lower trace). The G5PO woman showed 100% skewing. X-inactivation analysis of HUMANA was performed as in Example 1. Use of the highly polymorphic HUMANA locus afforded 91% of individuals informative for the X inactivation assay method.

The data are also presented in graphical form (FIG. 2). X-inactivation values are reported as the percentage of activity of the more-active alleles; thus, the data range is 50% to 100%, inclusive.

Example 4

Inheritance Pattern

Although the method of the invention does not require knowledge of the chromosomal locus of the molecular trait associated with high spontaneous pregnancy loss, such information may provide additional specificity to the method, particularly in combination with the use of labeled polynucleotide probes.

Pedigree analysis of one large family with a high incidense of RSA showed that all affected females were born to affected mothers; there was no male-to-female transmission, nor were there "isolated" cases (i.e., affected female child but nonaffected mother).

Because of this inheritance pattern, we tested an inheritance model of a fully penetrant monogenic X-linked dominant trait causing inactivation of the X chromosome harboring this trait. This involved an X-chromosome linkage search using 27 variable repeats spaced on an average of 10 cM apart on the X chromosome. Markers were typed on the ABI autosequencer, by use of fluorescent multiplex analysis.

Two-point linkage analysis were performed, and LOD scores were computed. A statistically significant LOD score (>2 for X-linked disorders) was obtained for marker DXS1108 in chromosome locus Xq28.

Further testing of markers in Xq28 showed that an intronic CA repeat in intron 13 of F8C suggested a lack of inheritance of alleles bextwen all informative affected female family members, suggestive of a deletion. The highest two-point maximum LOD score (Zmax) w3as observed for marker F8C between the trait and this putative deletion (Zmax=6.92 at theta=0). All females who carried the deletion (either by noniheritance of F8C or linkage to DXS1108, or both) showed highly skewed X inactivation (at least 95%). In addition, all the females scored as "unaffected" did not inherit the deleted X chromosome.

No other marker outside the Xq28 region showed a positive LOD score. Other studies identified the proximal boundaries of the deletion mutation between introns 19 and 22 of F8C, while the distal boundaries of the deletion were in a 800-kb interval upstream of the 5' end of F8C.

General Conclusions

The present X chromosome inactivation assay affords a screening test by which female carriers of X-linked recessive lethal defects producing recurrent spontaneous abortion can be identified. By continuing to monitor women with RSA and their extended family members, the individual causative genes can be identified. The X-chromosome assay method should become an important diagnostic tool in the clinical evaluation of women with RSA, as secondary skewed X inactivation will be the common denominator by which carriers of X-linked recessive lethal traits can be identified.

We claim:

1. A screening test for identifying female carriers of a X chromosome-linked recessive lethal genetic defect leading to recurrent spontaneous pregnancy loss in said females, comprising determining the frequency of highly skewed X chromosome inactivation in female patients compared to control females, said X chromosome inactivation analyses being conducted on DNA from test cells derived from said women.

2. The test of claim 1 wherein said highly skewed X chromosome inactivation is defined as the preferential use of one chromosome in at least 90% of said test cells.

3. The test of claim 1, wherein the molecular locus of said genetic defect maps to the Xq28 region of the chromosome.

4. The test of claim 1, wherein said test cells are peripheral blood leukocytes.

5. The test of claim 1, wherein said cells are oral mucosal cells.

6. The test of claim 1, wherein said cells are muscle biopsy cells.

7. The test of claim 1, wherein said X chromosome inactivation analyses are carried out by fluorescent PCR.

* * * * *

UNITED STATES PATENT AND TRADEMARK OFFICE
CERTIFICATE OF CORRECTION

PATENT NO.    : 6,268,145 B1                                      Page 1 of 1
DATED         : July 31, 2001
INVENTOR(S)   : Eric P. Hoffman, Mark C. Lanasa and W. Allen Hogge It is certified that error appears in the above-identified patent and that said Letters Patent is hereby corrected as shown below:

<u>Column 1,</u>
Line 12, before "BACKGROUND OF THE INVENTION", add the words:

-- This invention was made, in part, with Government support (R01 HD 37148 and R01 HD 38126 from the National Institutes of Health, USPHS), and the Government retains certain rights in this patent. --

Signed and Sealed this

Twenty-ninth Day of July, 2003

JAMES E. ROGAN
*Director of the United States Patent and Trademark Office*